United States Patent
Huttner et al.

[11] Patent Number: 6,052,436
[45] Date of Patent: Apr. 18, 2000

[54] RADIATION THERAPY DEVICE EMPLOYING CAM PIN AND CAM GROOVE GUIDING SYSTEM FOR CONTROLLING MOVEMENT OF LINEAR MULTI-LEAF COLLIMATOR LEAVES

[75] Inventors: James J. Huttner, Sylvania, Ohio; Andrew J. Milligan, Berwyn, Pa.

[73] Assignee: Bionix Development Corporation, Toledo, Ohio

[21] Appl. No.: 09/116,107

[22] Filed: Jul. 15, 1998

Related U.S. Application Data

[60] Provisional application No. 60/052,660, Jul. 16, 1997.

[51] Int. Cl.7 ........................................... G12K 1/04
[52] U.S. Cl. ........................ 378/152; 378/65; 250/505.1
[58] Field of Search ........................ 378/62, 152, 147, 378/150, 153; 250/505.1

[56] References Cited

U.S. PATENT DOCUMENTS

| | | |
|---|---|---|
| D. 387,170 | 12/1997 | Schuster . |
| 1,574,884 | 3/1926 | Hendricks et al. . |
| 2,624,013 | 12/1952 | Marks . |
| 3,539,813 | 11/1970 | Resnick . |
| 3,777,124 | 12/1973 | Pavkovich . |
| 3,783,251 | 1/1974 | Pavkovich . |
| 4,233,519 | 11/1980 | Coad . |
| 4,739,173 | 4/1988 | Blosser et al. ........................ 378/152 |
| 4,754,147 | 6/1988 | Maughan et al. . |
| 4,794,629 | 12/1988 | Pastyr et al. . |
| 4,798,961 | 1/1989 | Augustsson . |
| 4,868,844 | 9/1989 | Nunan ........................ 378/152 |
| 4,987,309 | 1/1991 | Klasen et al. . |
| 5,019,713 | 5/1991 | Schmidt . |
| 5,099,505 | 3/1992 | Seppi et al. . |
| 5,115,139 | 5/1992 | Cotter . |
| 5,160,847 | 11/1992 | Leavitt et al. . |
| 5,166,531 | 11/1992 | Huntzinger . |
| 5,190,990 | 3/1993 | Eichmiller . |
| 5,233,990 | 8/1993 | Barnea . |
| 5,243,372 | 9/1993 | Carol . |
| 5,267,294 | 11/1993 | Kuroda et al. . |
| 5,269,305 | 12/1993 | Corol . |
| 5,285,785 | 2/1994 | Meyer . |
| 5,291,404 | 3/1994 | Kurokawa et al. . |
| 5,343,048 | 8/1994 | Pastyr . |
| 5,360,666 | 11/1994 | Eichmiller . |
| 5,368,543 | 11/1994 | Carol . |
| 5,395,299 | 3/1995 | Herrmann et al. . |
| 5,411,026 | 5/1995 | Carol . |
| 5,470,350 | 11/1995 | Buchholtz et al. . |
| 5,471,516 | 11/1995 | Nunan . |
| 5,537,454 | 7/1996 | Korver, II . |
| 5,657,369 | 8/1997 | Stein et al. . |
| 5,680,861 | 10/1997 | Rohling . |
| 5,757,881 | 5/1998 | Hughes ........................ 378/152 |

*Primary Examiner*—David P. Porta
*Assistant Examiner*—Drew A. Dunn
*Attorney, Agent, or Firm*—Emch, Schaffer, Schaub & Porcello Co., L.P.A.

[57] ABSTRACT

A conformal radiation therapy device is disclosed. A multi-leaf collimator is mounted adjacent the head of a linear accelerator. A pair of spaced guides which define predetermined cam grooves are supported by the patient table. The multi-leaf collimator includes a plurality of longitudinally slidable leaves. Each of the leaves includes a cam pin mounted in a respective cam groove. As the head and multi-leaf collimator rotate relative to the patient, the predetermined cam grooves acting through the cam pins slide the individual leaves to adjust a radiation window for controlling radiation to the patient.

13 Claims, 4 Drawing Sheets

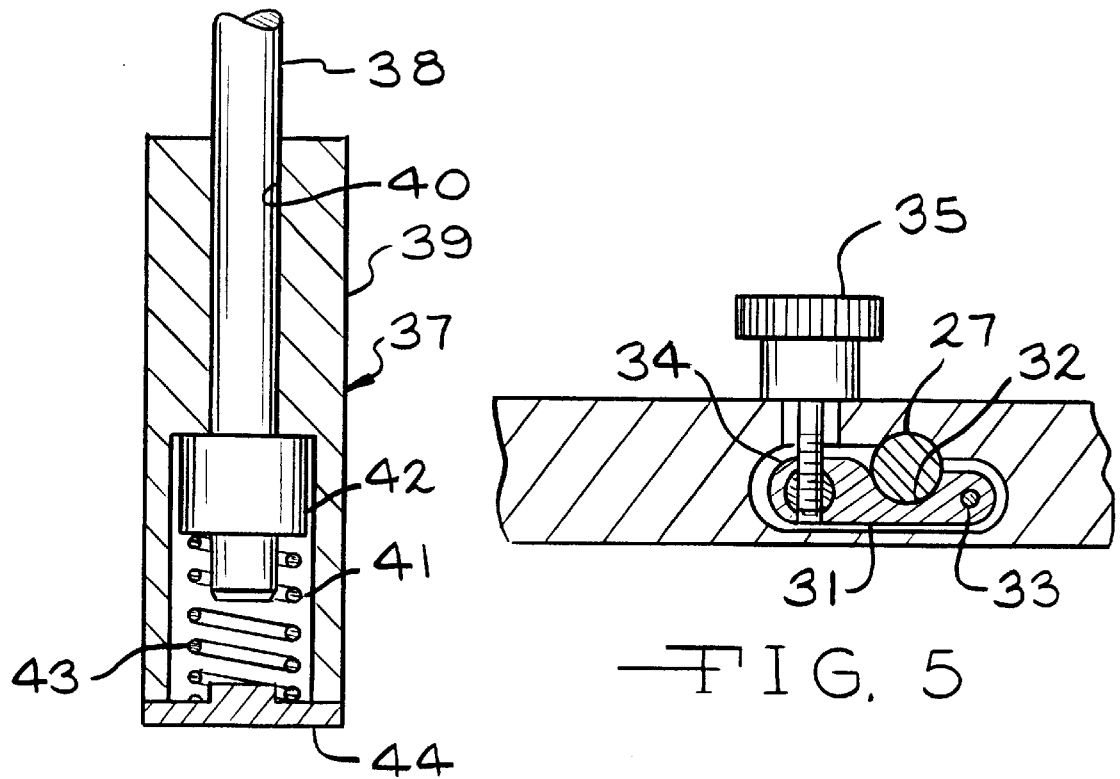
FIG. 4
FIG. 5
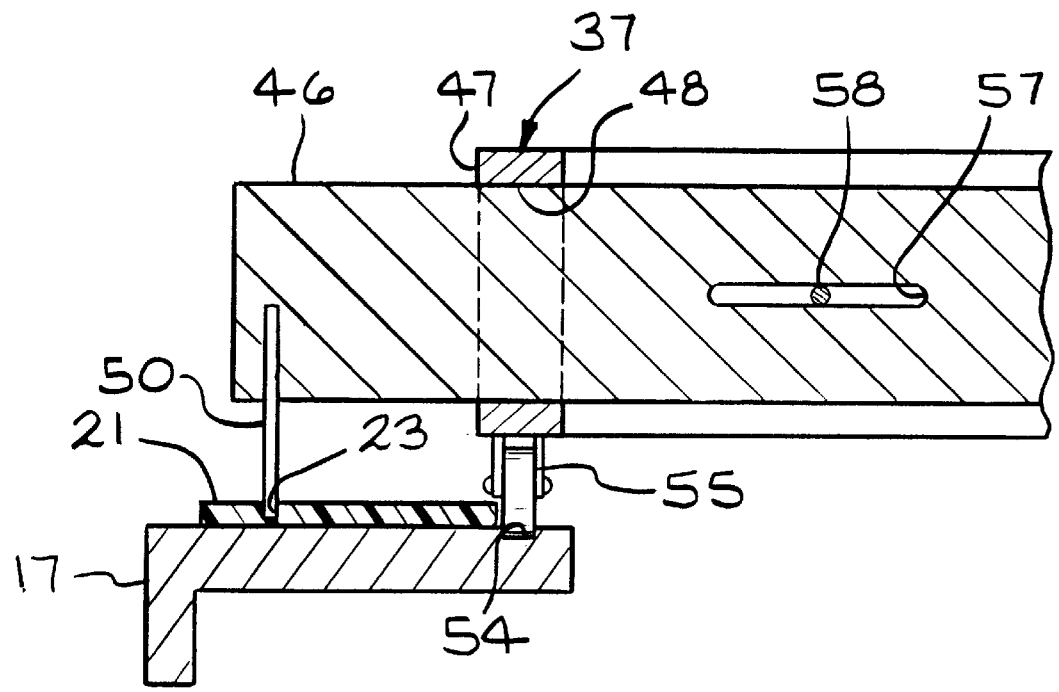
FIG. 6

RADIATION THERAPY DEVICE EMPLOYING CAM PIN AND CAM GROOVE GUIDING SYSTEM FOR CONTROLLING MOVEMENT OF LINEAR MULTI-LEAF COLLIMATOR LEAVES

This application claims the benefit of U.S. Provisional Application Ser. No.: 60/052,660 filed Jul. 16, 1997.

BACKGROUND

The present invention is directed to a conformal radiation therapy device for use in delivering radiation therapy for cancer treatment.

If a solid tumor is visualized using a three-dimensional treatment planning system such as one based on CT or MRI images, the tumor surface anatomy can be described by the data obtained. If this surface anatomy is then "viewed" through a slit-like opening, one views a section with a fixed "height" and a variable "width". As one scans about the tumor in a coronal planar section, the tumor width will seem to vary depending on the radial angulation of the view. In this way the "view" of the tumor will conform to the surface anatomy of the tumor as the slit-like opening is rotated about the patient.

Lineal accelerators are well known in the art and include collimators mounted in the head which emits the radiation. The collimator is used to adjust the area of the target. Multi-leaf collimators are also known in the art. These types of collimators are also mounted in the head or closely adjacent the head and are used to more specifically define the target areas desired to be treated. These multi-leaf collimators may be driven by microprocessors to adjust the target area.

SUMMARY OF THE INVENTION

The present invention is an improved conformal radiation therapy device which is mounted between the head of a linear accelerator and the patient. The patient is mounted on a support table in a predetermined position. The device includes a frame assembly connected to the patient support table. The frame assembly mounts a pair of spaced guides which define cam tracks. A multi-leaf collimator includes a plurality of collimator leaves having downwardly depending cams which are received in the cam tracks of the guides. A coupler assembly mounts the multi-leaf collimator to the head of the linear accelerator. The cams, which are controlled by the cam tracks in the guides move the collimator leaves in and out conforming to the "width" of the tumor as "viewed" through the defined collimator opening as the linear accelerator and the attached multi-leaf collimator rotates about the patient. In this way, the entire tumor surface is scanned by the multi-leaf collimator in a conformal fashion. Radiation therapy applied to the patient as the beam rotates about the patient, thus treats the tumor in a circumferential and conformal fashion, producing minimal normal tissue damage and maximizing treatment of the tumor.

DESCRIPTION OF THE DRAWINGS

FIG. 4 is an enlarged, fragmentary, cross-sectional view taken along the line 4—4 of FIG. 1;

FIG. 5 is an enlarged, cross-sectional view taken along the line 5—5 of FIG. 1; and FIG. 6 is an enlarged cross-sectional view taken along the line 6—6 of FIG. 2.

DETAILED DESCRIPTION OF THE PREFERRED EMBODIMENTS

Figure 1:
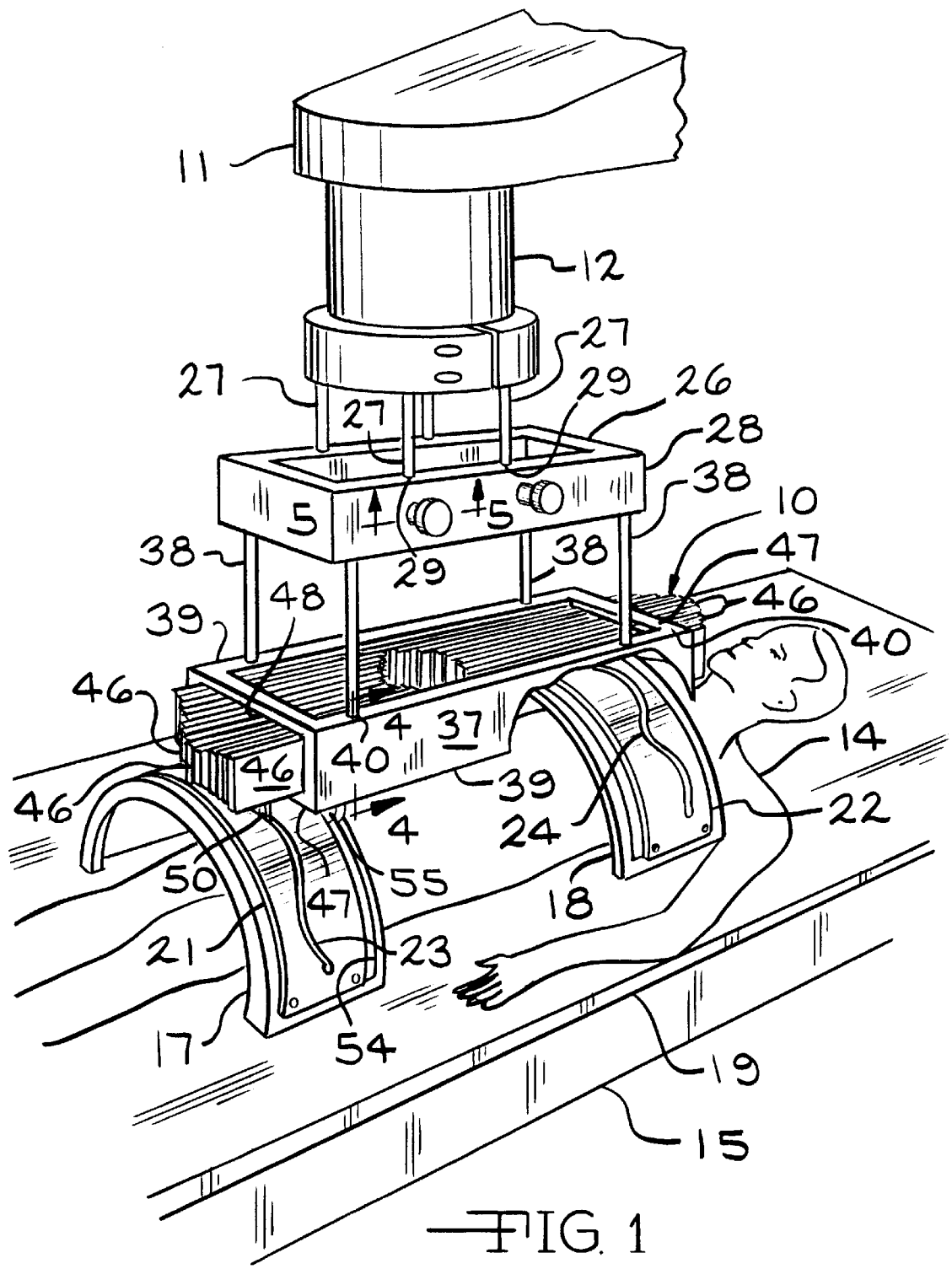
FIG. 1 is a perspective view of a conformal radiation therapy device, according to the present invention, in position to treat a patient.
Figure 2:
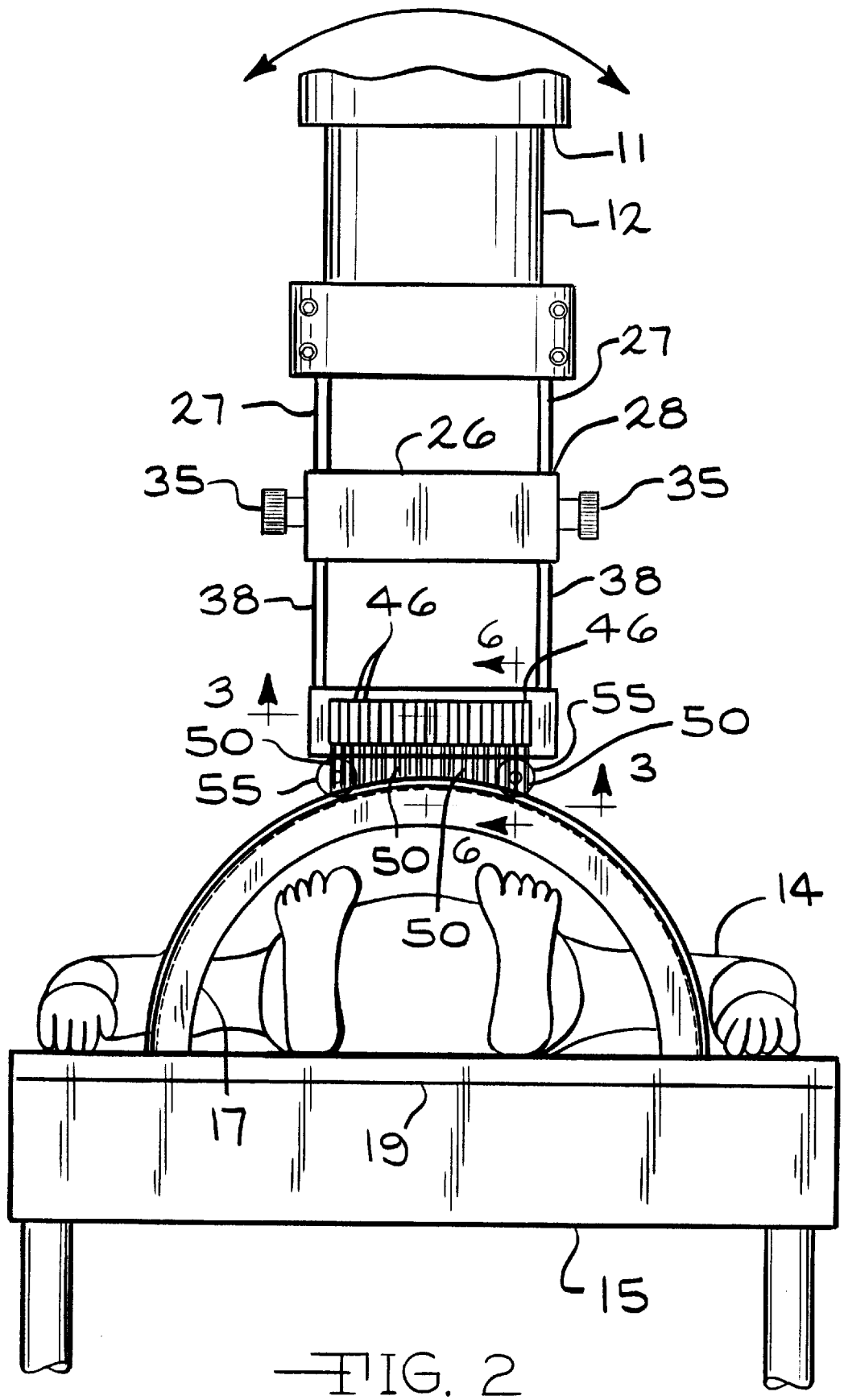
FIG. 2 is an end view of the conformal radiation therapy device as shown in FIG. 1.

Referring to FIGS. 1 and 2, a conformal radiation therapy device, according to the present invention is generally indicated by the reference number 10. A lineal accelerator 11 includes a head 12 which emits radiation. The head 12 normally has the capability of rotating 360° around a patient 14. In the present embodiment, the head is rotated through an accurate path of approximately 180°. In the present embodiment, the patient 14 is placed in a predetermined position on a patient support table 15. A pair of semi-circular tracking frames 17 and 18 are secured to the patient support table 15. Normally, a patient support base 19 is first mounted on the patient support table 15 and the tracking frames 17 and 18 are attached to the patient support base 19. The patient support base 19 must lock to the patient support table 15 during treatment so that there is no motion during treatment. Preferably, any movement should be less than 1 mm along all axes. The patient support base 19 must allow the patient 14 to be positioned reproducibly and be held securely throughout the treatment process. The spaced tracking frames 17 and 18 are locked securely to the patient support base 19 to form a structurally rigid unit throughout the treatment process. A pair of guide members 21 and 22 are arcuately shaped and mounted on the tracking frames 17 and 18, respectively. The guide members 21 and 22 are preferably constructed of a plastic material and define aligned cam grooves 23 and 24. The cam grooves 23 and 24 are preferably computer milled using data supplied from the CT or MRI simulation process. Tolerance in the milling process is normally within 0.001 inch.

A coupler assembly 26 is mounted by a plurality of rods 27 to the head 12 of the linear accelerator 11. The coupler assembly 26 includes a coupler frame 28 having openings 29 which receive the individual rods 27.

Referring to FIG. 5, each rod 27 is adjustable and is locked in place by a pivotable lock arm 31 which defines a recess 32 for receiving the rod 27. The lock arm 31 is pivoted on a pivot pin 33. A threaded shaft 34 is attached to the other end of the lock arm 31. The threaded shaft 34 extends from a knob 35. The knob 35 is rotated to pivot the lock arm 31 thereby releasing the rod 27 from the recess 32. In this matter, the coupler frame 28 may be vertically adjusted. When the coupler frame 28 is at its correct position, the knob 35 is rotated in the opposite direction moving the lock arm 31 tightly against the rod 37.

A multi-leaf collimator 37 is mounted below the coupler frame 28 by a plurality of rods 38. The multi-leaf collimator 37 includes spaced sides 39 having openings 40 which receive the lower ends of the rods 38. An enlarged opening 41 is coaxially defined below the openings 40. A nut 42 is threadably mounted on each of the bottom ends of the rods 38 and is received within the enlarged opening 41.

As shown in FIG. 4, a coil spring 43 is positioned within the enlarged opening 41 beneath the nut 42 in surrounding relationship to the rod 38. The coil springs 43 act as cushions for the weight of the multi-leaf collimator 37. Preferably caps 44 are mounted at the bottom of the enlarged openings 41 beneath the coil springs 43. A plurality of collimator leaves 46 are mounted for sliding movement within the multi-leaf collimator 37. The collimator 37 includes end panels 47 having end openings 48. The opposed end panels 47 extend between the sides 39. The collimator leaves 46 extend outwardly through the end openings 48 of the end panels 47. Each of the collimator leaves 46 includes a downwardly extending cam pin 50 which is received in a respective one of the cam grooves 23 and 24 defined by the guide members 21 and 22. The collimator leaves 46 are preferably constructed of lead alloys, tungsten, depleted uranium or similar materials. While the number of collimator leaves 46 varies, depending on the thickness of the leaves, normally 5 to 20 leaves 46 would be provided.

As shown in FIG. 1, the collimator leaves 46 define a radiation window or radiation jaw 51. The radiation window 51 varies as the head 12 of the linear accelerator 11 is rotated and the cam pins 50 move in the mated cam grooves 23 and 24. The shape of the radiation window 51 is changed to provide the proper "view" of the tumor in conformance with the surface anatomy of the tumor during rotation about the patient 14.

Referring to FIG. 6, the tracking frames 17 and 18 define a track recess 54 adjacent the respective guide members 21 and 22. A roller 55 is mounted beneath each corner of the multi-leaf collimator 37 adjacent the intersections of the sides 39 and the end panels 47. The rollers 55 ride in the recessed tracks 54 and transfer the weight of the multi-leaf collimator 37 to the patient support table 15.

Figure 3:
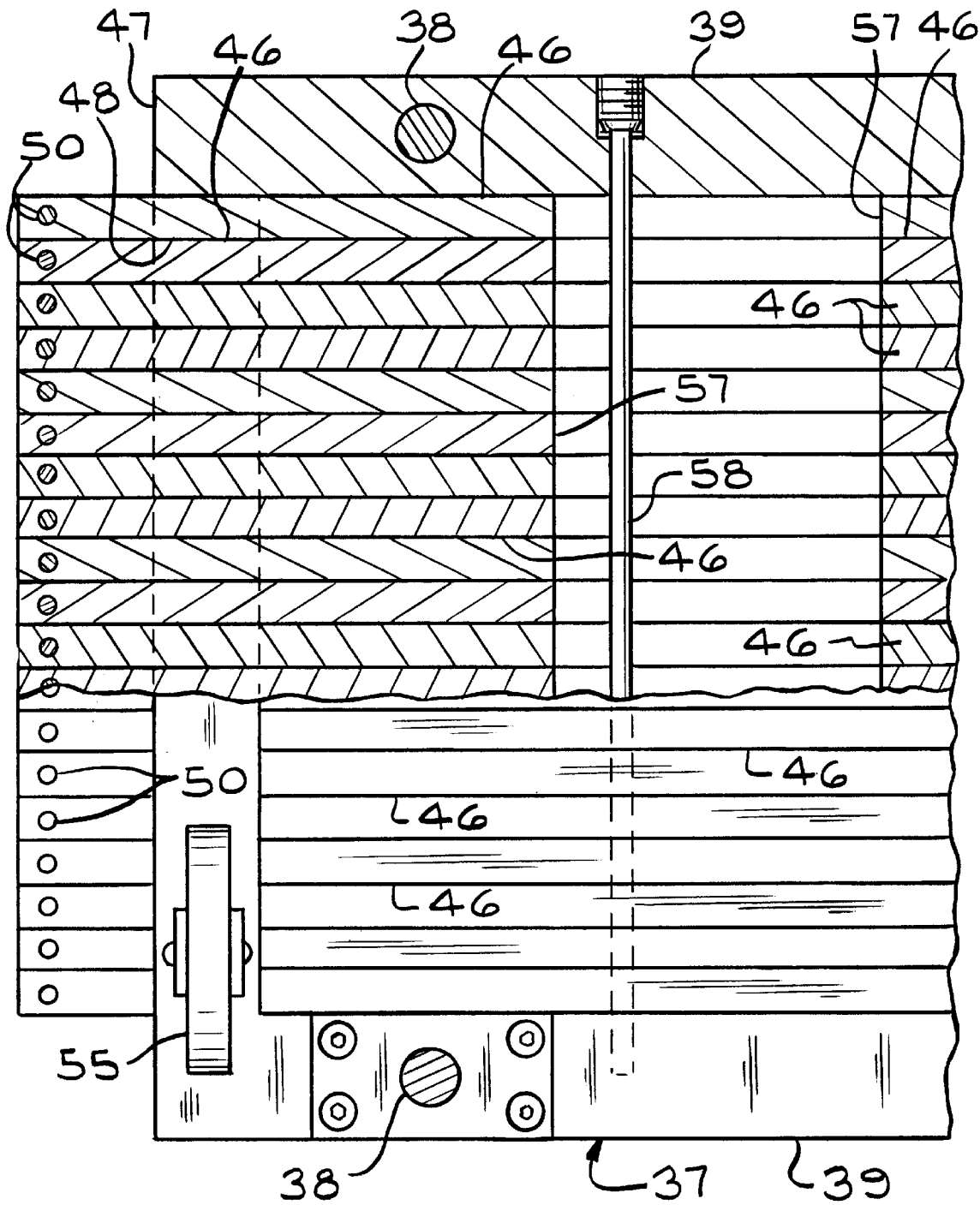
FIG. 3 is an enlarged partially cross-sectional view taken along the line 3—3 of FIG. 2.

Referring to FIG. 3, each of the collimator leaves 46 is preferably slotted to provide a longitudinally extending opening 57. A threaded support shaft 58 extends through the aligned openings 57 within the collimator leaves 46 between the respective spaced sides 39 of the multi-leaf collimator 37. The support shaft 58 prevents undesired movement of the collimator leaves 46 in a direction parallel to the longitudinally extending sides 39.

During use of the conformal radiation therapy device 10, according to the present invention, the patient has previously been placed in a defined positioned. The tumor is visualized using a three-dimensional treatment planning system such as known CT or MRI images. Because the tumor surface anatomy varies as a linear accelerator radiation head is rotated, the data collected from the simulator generates the desired cam grooves 23 and 24 to be placed in the guide members 21 and 22. Rotation of the head 12 moves the collimator leaves 46 by way of the cam pins 50 and the cam grooves 23 and 24 to provide the desired radiation window 51 to properly treat the patient with radiation. Proper treatment directs the radiation to the tumor and not to surrounding tissue.

Many revisions may be made to the above described embodiments without departing from the scope of the invention or from the following claims.

We claim:

1. A conformal radiation therapy device for use with a patient table and a linear accelerator having a rotatable head, said device including a multi-leaf collimator positioned below such head, a pair of spaced guides for mounting on said patient table, said guides defining a cam groove, said multi-leaf collimator including a plurality of collimator leaves which are mounted for individual longitudinal movement and which define a radiation window below said head, each of said collimator leaves including a cam pin mounted in said cam groove, whereby rotation of said multi-leaf collimator moves said cam pins along the path defined by said cam groove to move said collimator leaves and adjust said radiation window.

2. A conformal radiation therapy device, according to claim 1, including a support base mounted on said patient table.

3. A conformal radiation therapy device, according to claim 2, including a pair of spaced tracking frames mounted on said support base and one of said guides mounted on each of said tracking frames.

4. A conformal radiation therapy device, according to claim 1, including a coupler assembly depending from said rotatable head, said multi-leaf collimator mounted beneath said coupler assembly.

5. A conformal radiation therapy device, according to claim 4, wherein said multi-leaf collimator includes a rectangular frame including spaced sides and a pair of opposed end panels between said spaced sides, a plurality of support members extending between said coupler assembly and said frame and cushioning means adjacent said support members.

6. A conformal radiation therapy device, according to claim 5, wherein said support members comprise a plurality of support rods and said cushioning means comprise a plurality of coil springs surrounding said support rods.

7. A conformal radiation therapy device, according to claim 1, including a pair of spaced tracking frames mounted above said patient table, said tracking frames mounting said spaced guides and defining a pair of spaced tracks, rollers mounted on said multi-leaf collimator, said rollers positioned for movement along said spaced tracks.

8. A conformal radiation therapy device, according to claim 4, including a plurality of support rods extending between said rotatable head and said coupler assembly.

9. A conformal radiation therapy device, according to claim 8, including means for adjusting the spacing between said rotatable head and said coupler assembly.

10. A guide for a conformal radiation therapy device for use with a linear accelerator having a rotatable head and a multi-leaf collimator positioned below such head, said multi-leaf collimator having a plurality of collimator leaves which are mounted for individual longitudinal movement and which define a radiation window below said head, each collimator leaf including a cam pin, said guide comprising at least one guide defining a cam groove positioned adjacent said multi-leaf collimator, said cam groove being disposed to engage said cam pin on said collimator leaves, whereby rotation of said multi-leaf collimator moves said cam pins along the path defined by said cam grooves to move said collimator leaves and adjust said radiation window.

11. The guide of claim 10 wherein a pair of spaced guides that each define a cam groove are positioned adjacent said multi-leaf collimator, said collimator leaves having a cam pin that engages the cam groove in each guide.

12. A method for varying the radiation window presented by a multi-leaf collimator comprising the steps of:

mounting the collimator leaves for individual longitudinal movement;

engaging said collimator leaves with at least one guide means whereby said guide means causes said collimator leaves to move in a longitudinal direction to vary said radiation window; and wherein said collimator leaves have a cam pin for engaging a cam groove in the guide means.

13. The method of claim 12 in which said multi-leaf collimator is rotated to cause said cam pins to interact with said cam groove to cause said collimator leaves to move in a longitudinal direction to vary said radiation window.

* * * * *